United States Patent
Lee et al.

(10) Patent No.: US 9,084,721 B2
(45) Date of Patent: *Jul. 21, 2015

(54) RACECADOTRIL LIQUID COMPOSITIONS

(71) Applicant: McNeil-PPC, Inc.

(72) Inventors: Der-Yang Lee, Flemington, NJ (US); Tusharmouli Mukherjee, Skillman, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/929,975

(22) Filed: Jun. 28, 2013

(65) Prior Publication Data

US 2014/0005261 A1 Jan. 2, 2014

Related U.S. Application Data

(60) Provisional application No. 61/665,458, filed on Jun. 28, 2012, provisional application No. 61/787,496, filed on Mar. 15, 2013.

(51) Int. Cl.
| | |
|---|---|
| *A61K 45/06* | (2006.01) |
| *A61K 47/40* | (2006.01) |
| *A61K 31/223* | (2006.01) |
| *A61K 9/00* | (2006.01) |
| *A61K 31/265* | (2006.01) |

(52) U.S. Cl.
CPC .............. *A61K 9/0053* (2013.01); *A61K 9/0095* (2013.01); *A61K 31/223* (2013.01); *A61K 31/265* (2013.01); *A61K 45/06* (2013.01); *A61K 47/40* (2013.01)

(58) Field of Classification Search
CPC .. C07D 231/14; C07D 403/10; C07D 233/70; C07D 233/90; C07D 233/68; C07D 233/64; C07D 249/08; C07D 401/06; C07D 249/10; C07D 401/04; C07D 249/04; C07D 257/04; C07D 401/12; C07D 405/12; C07D 213/64; C07D 253/08; C07D 271/04; C07D 271/08; C07D 403/14; C07D 409/14; A61K 45/06; A61K 47/40; A61K 31/724; A61K 9/08; A61K 9/0053; A61K 9/0095

See application file for complete search history.

(56) References Cited

U.S. PATENT DOCUMENTS

| 7,034,013 B2 * | 4/2006 | Thompson et al. ............. 514/58 |
| 2004/0115258 A1 * | 6/2004 | Stroppolo et al. ............ 424/465 |
| 2005/0250738 A1 * | 11/2005 | Mosher et al. .................. 514/58 |

FOREIGN PATENT DOCUMENTS

| EP | 1563848 A1 * | 8/2005 |
| EP | 2462922 A1 | 6/2012 |
| WO | WO 9504528 A2 * | 2/1995 |
| WO | WO 01/97801 A2 | 12/2001 |
| WO | 2014/005021 A1 | 1/2014 |
| WO | 2014/150651 A1 | 9/2014 |
| WO | 2014/150660 A1 | 9/2014 |

OTHER PUBLICATIONS

Thorsteinn, Loftsson "Effect of cyclodextrins on the chemical stability of drugs in aqueous solutions", Drug Stability, Radcliff Medical Press, Abingdon, GB. vol. 1, No. 1, Jan. 1, 1995, pp. 22-33, XP002080429.

Tambe, Vrushali, et al., "Comparative Study of Different Solubility Enhancement Techniques and Various Excipients on Solubility and Dissolution Rate of Racecadotril". Indian Journal of Novel Drug Delivery, 6(1), Jan.-Mar. 2014, 74-80.

Search Report—PCT/US2014/023882 dated Jun. 5, 2014.

Pitha, J. et al, "Hydroxypropyl-beta-cyclodextrin: preparation and characterization; effects on solubility of drugs", International Journal of Pharmaceutics, Elsevier BV, NL, vol. 29, No. 1, Mar. 1, 1986, pp. 73-82, XP025502232, ISSN: 0378-5173, DOI: 10.1016/0378-5173(86)90201-2 [retrieved on Mar. 1, 1986] the whole document in particular abstract p. 79, col. 2, last paragraph-p. 81, col. 1, paragraph first table 1. Discussion.

Semalty, Mona et al. "Cyclodextrin inclusion complex of racecoditril: effect of drug-[beta]-cyclodextrin ratio and the method of complexation", Current Drug Discovery Technologies., vol. 11, No. 2, Jun. 1, 2014, pp. 154-161, XP009183081, ISSN: 1875-6220 the whole document.

Search Report PCT/US2014/071906 dated Mar. 20, 2015.

* cited by examiner

*Primary Examiner* — Misook Yu
*Assistant Examiner* — Kauser M Akhoon
(74) *Attorney, Agent, or Firm* — Laura A. Donnelly

(57) ABSTRACT

A liquid composition comprising racecadotril and cyclodextrin.

18 Claims, No Drawings

RACECADOTRIL LIQUID COMPOSITIONS

CROSS REFERENCE TO RELATED APPLICATIONS

This application claims the benefit of U.S. Provisional Application No. 61/665,458. filed on Jun. 28, 2012 and U.S. Provisional Application No. 61/787,496. filed on Mar. 15, 2013. which are incorporated by reference.

BACKGROUND OF THE INVENTION

1. Field of the Invention

The present invention relates to liquid compositions. More particularly, the present invention relates to liquid compositions containing racecadotril and the method of making said compositions.

2. Related Background Art

Diarrhea is an intestinal disorder that is characterized by an increase in the frequency of watery bowel movements. It may result from a variety of causes including bacteria or viral induced diarrhea. Food intolerance caused by allergy or the consumption of foods such as fatty or spicy foods may result in diarrhea. Food poisoning may also lead to diarrhea. In some instances, diarrhea may be a symptom of other conditions and diseases.

Diarrhea is symptomatic of an intestinal or other bodily function disorder. Various prescription and nonprescription products can be taken for relief. However, many of these products provide relief with some side effects.

Racecadotril is also used in the treatment of diarrhea. It reduces (i) hypersecretion of water and electrolytes into the intestinal lumen, (ii) the incidence and duration of acute diarrhea and (iii) diarrhea-associated symptoms.

Presently, racecadotril is available in solid oral dosage forms.

SUMMARY OF THE INVENTION

The present invention is directed to a liquid composition comprising racecadotril and cyclodextrin.

In one embodiment, the inventive composition comprises about 0.01 wt. % to about 24.0 wt. % racecadotril and about 1 wt. % to about 95 wt. % of a cyclodextrin, wherein each wt. % is based upon 100 ml of the composition.

The present invention also includes a method for treating a subject experiencing diarrhea comprising the step of orally administering to the subject a composition comprising racecadotril and cyclodextrin.

DETAILED DESCRIPTION OF THE INVENTION

As used herein, "stable" refers to a liquid composition substantially free of chemical degradation of racecadotril or substantial color change. In one embodiment, the total chemical degradant products of racecadotril should be less than 0.2 percent by weight (wt. %), e.g. less than 0.1 wt. % based on the total wt. % of racecadotril when stored at 3 months and 40° C. In another embodiment, the total chemical degradant products of racecadotril should be less than 0.2 percent by weight (wt. %), e.g. less than 0.1 wt. % based on the total wt. % of racecadotril when stored at 6 months and 40° C.

The percent degradation products are determined by calculating the % peak area of the degradation product peak areas relative to the peak areas of the Racecadotril peaks in the HPLC chromatograms. In one embodiment, the total chemical degradant products of racecadotril should be less than 0.5% of racecadotril, e.g., less than 0.2% based on of the total % of racecadotril when stored at 3 months and 40° C.

The present invention is a liquid composition comprising racecadotril and cyclodextrin.

Racecadotril's efficacy in reducing the symptoms of diarrhea have been demonstrated in various studies. One of the benefits of using racecadotril over other remedies is that in comparative trials racecadotril was shown to have fewer adverse events such as post-treatment constipation.

In the present invention, the racecadotril is included in a stable liquid composition.

Racecadotril is a compound with low water solubility, making it difficult to formulate into liquid compositions. However, oral liquid compositions are the most preferred dosage form for administering medications to the pediatric population.

In one embodiment, a RS racemic form of racecadotril is used. In another embodiment, a R form of racecadotril is used.

Racecadotril is included in the liquid composition in an amount from about 0.01 grams to about 0.5 grams per 100 ml of the liquid composition. Preferably, the racecadotril is about 0.05 grams to about 0.4 grams, and more preferably, about 0.1 grams to about 0.3 grams per 100 ml of the liquid composition. In one embodiment, the racecadotril is about 0.25 grams per 100 ml of liquid composition.

In one embodiment, the viscosity of the liquid composition is from about 1 to about 500 centipoise at room temperature (25° C.) measured using a Brookfield Viscometer.

The pH of the liquid composition is from about 1 to about 6. Preferably, the pH is about 3 to about 5. More preferably, the pH is about 4.5.

In one embodiment, a buffering system may be included to maintain the pH at the value or in the desired range. The buffer may be a citrate, an acetate, a phosphate, or mixtures thereof. Preferably, an acetate buffer is used.

In one embodiment the racecadotril is dissolved into the liquid composition.

Cyclodextrins are compounds used in a wide variety of products, which include pharmaceutical, food, consumer and chemical products. They are synthesized from starch via an enzymatic reaction.

Suitable cyclodextrins include, for example, alpha-cyclodextrin, beta-cyclodextrin, gamma-cyclodextrin, hydroxypropyl-beta-cyclodextrin, hydroxypropyl-gamma-cyclodextrin, or mixtures thereof.

In one embodiment, the cyclodextrin is hydroxypropyl-beta-cyclodextrin. One source of hydroxypropyl-beta-cyclodextrin is CAVASOL W7 available from International Speciality Products Corporation (ISP).

In another embodiment, the cyclodextrin is a sulfobutyl ether derivative of β-cyclodextrin, sold under the tradename CAPTISOL available from Captisol.

The cyclodextrin is included in the composition in an amount from about 1 grams to about 70 grams per 100 ml of the liquid composition. Preferably, the cyclodextrin is about 5 grams to about 60 grams, and more preferably, about 5 grams to about 50 grams per 100 ml of the liquid composition.

In one embodiment, the cyclodextrin is from about 40 grams to about 60 grams per 100 ml of the liquid composition.

In another embodiment, the cyclodextrin is from about 15 grams to about 30 grams per 100 ml of the liquid composition.

The liquid composition also has water. Water is the solvent that fills the gap after all other components have been added. The amount of water that is included varies because the water is added to bring the composition up to a desired volume amount.

Optionally, a variety of ingredients may be included in the liquid composition of the present invention.

For example, propylene glycol may be included in the liquid composition. Propylene glycol has many uses, such as for example a moisturizer in food and medicines, and as a solvent for food colorings and flavorings. It is a colorless, nearly odorless, clear, viscous liquid with a faintly sweet taste, hygroscopic and miscible with water, acetone, and chloroform.

Any coloring agent suitable for use in a food or pharmaceutical product may be used in the present inventive composition. Typical coloring agents include, for example, azo dyes, quinopthalone dyes, triphenylmethane dyes, xanthene dyes, indigoid dyes, iron oxides, iron hydroxides, titanium dioxide, natural dyes, and mixtures thereof. More specifically, suitable colorants include, but are not limited to patent blue V, acid brilliant green BS, red 2G, azorubine, ponceau 4R, amaranth, D&C red 33. D&C red 22. D&C red 26. D&C red 28. D&C yellow 10, FD&C yellow 5. FD&C yellow 6. FD&C red 3. FD&C red 40. FD&C blue 1. FD&C blue 2, FD&C green 3. brilliant black BN, carbon black, iron oxide black, iron oxide red, iron oxide yellow, titanium dioxide, riboflavin, carotenes, antyhocyanines, turmeric, cochineal extract, clorophyllin, canthaxanthin, caramel, betanin, and mixtures thereof.

Similarly, a flavor may be included in the liquid composition. The amount of flavor added to the composition will be dependent upon the desired taste characteristics.

The composition may contain other ingredients or components, such as aromas; sweeteners such as, sorbitol, high fructose corn syrup, sugar, and high intensity sweeteners such as sucralose, aspartame and saccharine and the like; viscosity modifiers such as xanthan gum; preservatives such as sodium benzoate NF, buffers such as citric acid and/or sodium chloride; surfactants such as polysorbate 80 and/or sodium lauryl sulfate or mixtures thereof.

In one embodiment, the inventive liquid composition includes about 0.1 wt. % to about 0.3 wt. % racecadotril and about 40 wt. % to about 65 wt. % cyclodextrin, wherein each wt. % is based upon 100 ml of the composition.

In another embodiment, the inventive liquid composition includes about 0.1 wt. % to about 0.3 wt. % racecadotril and about 10 wt. % to about 40 wt. % cyclodextrin, wherein each wt. % is based upon 100 ml of the composition.

The solubility of the racecadotril in the inventive composition is about 1.5 to about 4.0 mg/ml.

The liquid composition of the present invention may be made by any method known to those skilled in the art so long as it results in the desired composition.

Suitable methods include, for example, combining each ingredient in a mixing kettle, where the ingredients may be added sequentially or in any manner so long as the intended result is achieved. Moreover, the mixing action should be sufficient to incorporate each ingredient into the composition.

In one embodiment the liquid of the present invention comprises a second active ingredient. The second active ingredient may be, for example, present in a suspended state, or may be solubilized in the liquid composition. In one embodiment, the second active ingredient is a digestive health active ingredient may be, for example, laxatives, antacids, proton pump inhibitors, anti-gas agents, antiemetics, H2 blockers, a second antidiarrheal agent, and the like. In one embodiment, the second active ingredient is microencapsulated.

Suitable anti-gas agents include but are not limited to simethicone.

Suitable additional antidiarrheal agents include but are not limited to loperamide.

The inventive liquid composition may be delivered in any suitable delivery system. For example, in one embodiment, the liquid composition is delivered orally. In another embodiment, the composition is a liquid oral dosage form. In still another embodiment, a soft shell solid dosage form is used to deliver the liquid composition. In still yet another embodiment, a hard shell solid dosage form is used to deliver the liquid composition. In still yet another embodiment, a tablet dosage form is used to deliver the liquid composition.

The present invention also includes a method for treating a subject experiencing diarrhea comprising the step of orally administering to the subject a composition comprising racecadotril and cyclodextrin.

The following example is provided to further illustrate the compositions and methods of the present invention. It should be understood that the present invention is not limited to the examples described.

EXAMPLE 1

Racecadotril Oral Liquid Formulation

The composition for an oral racecadotril liquid is shown in Table 1. Utilizing the materials in Table 1. the following mixing steps were used:

Step 1: A solution of was formed by mixing the purified water and hydroxypropyl beta-cyclodextrin in a suitable vessel with a laboratory mixer.

Step 2: The racecadotril was added to the solution in Step 1 and mixed in a laboratory shaker for at least 12 hours and a clear solution was formed.

Step 3: The citric acid, sorbitol solution, high fructose corn syrup, and sodium chloride was mixed to form a solution and mixed using a laboratory mixer until dissolved.

Step 4: A separate mixture was prepared by mixing the flavor into the polyethylene glycol 400 in a suitable vessel. This mixture was then mixed with the solution from Step 3 and diluted to volume with purified water.

TABLE 1

Racecadotril Oral Liquid Composition (2.5 mg/g)

| Ingredient | % Weight by Weight |
| --- | --- |
| Racecadotril | 0.25 |
| Hydroxypropyl beta-cyclodextrin[1] | 7.00 |
| Citric Acid | 0.21 |
| Sorbitol (70% weight/weight) | 17.50 |
| High Fructose Corn Syrup (42% weight/weight) | 49.75 |
| Sodium Chloride | 0.25 |
| Polyethylene Glycol 400 | 0.50 |
| Flavor | 0.10 |
| Purified Water | 24.44 |
| Total | 100.0* |

[1]Commercially available from the ISP as CAVASOL W7

EXAMPLE 2

Concentrated Racecadotril Aqueous composition

Three formulations of racecadotril in an aqueous buffer of acetate were prepared and three formulations of racecadotril in an aqueous buffer of citrate were prepared. These formulations were prepared utilizing a mixture of racecadotril in the Sulfobutyl ether derivative of β-cyclodextrin (Captisol®) and are shown in Table 2.

TABLE 2

Racecadotril Sulfobutyl Ether Derivative of β-cyclodextrin Based Aqueous Compositions

| | Solvent System | | | Actual Composition | | | | |
|---|---|---|---|---|---|---|---|---|
| Lot # | Captisol (w/v) | Acetate Buffer (mL) | Racecadotril by Assay (mg/mL) | Captisol (g) | Acetate Buffer (mL) | Captisol (w/w %) | Acetate Buffer (w/w %) | Racecadotril (w/w %) |
| Formula 1 | 60% | 100 | 2.62 | 59.9972 | 54.0 | 52.49 | 47.25 | 0.26 |
| Formula 3 | 70% | 100 | 2.41 | 70.0018 | 48.0 | 59.18 | 40.58 | 0.24 |
| Formula 5 | 78% | 100 | 2.26 | 80.0035 | 54.6 | 59.30 | 40.47 | 0.23 |

| | Solvent System | | Actual Racecadotril | Actual Composition | | | | |
|---|---|---|---|---|---|---|---|---|
| Lot # | Captisol (w/v) | Citrate Buffer | by Assay (mg/mL) | Captisol (g) | Citrate Buffer (mL) | Captisol (w/w %) | Citrate Buffer (w/w %) | Racecadotril (w/w %) |
| Formula 2 | 60% | 100 | 2.43 | 60.0120 | 66.0 | 47.51 | 52.25 | 0.24 |
| Formula 4 | 69% | 100 | 2.39 | 70.0016 | 62.0 | 52.90 | 46.86 | 0.24 |
| Formula 6 | 80% | 50 | 1.92 | 39.9954 | 33.0 | 54.69 | 45.12 | 0.19 |

Utilizing the materials in TABLE 2. the following mixing steps were taken to form the solutions.

Step 1: In a suitable glass bottle, the Captisol® were weighed, mixed and prepared as 60%, 70% and 78% in pH 4.5 acetate buffers, respectively (Formulae 1, 3 and 5). Also, the Captisol® were weighed and prepared as 60%, 69% and 80% in pH 4.5 citrate buffers, respectively (Formulae 2, 4 and 6).

Step 2: The pH of each bottle was adjusted to pH 4.5 with either glacial acetic acid (17.4 M) or citric acid (3 M).

Step 3: The Racecadotril was slowly added to each bottle in Step 2. utilizing the vortex mixer to mix for 5 minutes, and then placed each bottle into a laboratory shaker and mixed for 24 hours until a solution was formed.

Stability of Racecadotril in Aqueous Solutions

For comparative purposes, the stability of racecadotril was tested at room temperature and at 40° C.

TABLE 3

Stability of Racecadotril in Water

| Time | Racecadotril (%) in Water at Room Temperature (%) | Racecadotril (%) in Water at 40° C. |
|---|---|---|
| Initial | 74.88 | 78.88 |
| 12 Hours | 44.9 | N/A |
| 1 Week | 1.0 | 0 |
| 2 Weeks | 0.0 | 0.2 |
| 3 Weeks | N/A | N/A |

These results show that at room temperature and at 40° C. conditions, racecadotril is unstable after 12 hours. Moreover, at 1 week, racecadotril is present at less than 1%.

Stability of Racecadotril in Buffer Solutions

For comparative purposes, the stability of racecadotril was analyzed when solubilized in pH 4.5 Acetate buffer and pH 4.5 Citrate buffer (Table 4).

TABLE 4

Stability of Racecadotril in Buffer

| Time | Racecadotril in pH 4.5 Acetate Buffer at 40° C. (% Racecadotril) | Racecadotril in pH 4.5 Citrate Buffer at 40° C. (% Racecadotril) |
|---|---|---|
| Initial | 99.86 | 99.74 |
| 12 Hours | 99.69 | 99.63 |
| 1 Week | 96.7 | 95.3 |
| 2 Weeks | 93.3 | 91.2 |
| 3 Weeks | 91.5 | 89.0 |
| 4 Weeks | 88.0 | 85.4 |

The data shows at 40° C. and 4 weeks that although the stability is somewhat compromised, it is more stable in a buffer than in water. The data also demonstrates that racecadotril is more soluble in buffer than in water.

Stability of Racecadotril in Beta-Hydroxypropyl-Cyclodextrin (Beta-HPCD)

Formulations of racecadotril in beta-hydroxypropyl-cyclodextrin were evaluated (Table 5).

TABLE 5

Stability of Racecadotril in Beta-Hydroxypropyl-Cyclodextrin (Beta-HPCD)

| Time | Racecadotril in Beta-HPCD at 40° C. (%) without pH Adjustment, Acetate Buffer | Racecadotril in Beta-HPCD at 40° C. (%) with pH Adjustment to 4.5, Acetate Buffer | Racecadotril in Beta-HPCD at 40° C. (%) without pH Adjustment, Citrate Buffer | Racecadotril in Beta-HPCD at 40° C. (%) with pH Adjustment to 4.5, Citrate Buffer |
|---|---|---|---|---|
| Initial | 99.5 | 99.58 | 99.3 | 99.58 |
| 12 Hours | 96.9 | 98.07 | 96.9 | 98.12 |
| 1 Week | 94.1 | 96.16 | 93.6 | 96.20 |
| 2 Weeks |  | 92.7 |  | 92.91 |
| 3 Weeks |  | 88.95 |  | 89.59 |
| 4 Weeks |  | 85.84 |  | 86.80 |

The data shows that the stability is similar to that in buffers alone, but higher solubility was achieved utilizing the Beta-HPCD.

Stability of Racecadotril in Sulfobutyl Ether Derivative of β-cyclodextrin[1] Solution The stability of samples prepared above in Example 2 utilizing Sulfobutyl ether derivative of β-cyclodextrin (Captisol®) solutions was analyzed. The data is shown in Table 6.

TABLE 6

Stability Data of Racecadotril in Sulfobutyl Ether Derivative of β-cyclodextrin based Aqueous Solution (3 month @ 40° C.)

|  | Formula 1 | Formula 2 | Formula 3 | Formula 4 | Formula 5 | Formula 6 |
|---|---|---|---|---|---|---|
| Racecadotril (%) | 90.95 | 89.23 | 91.32 | 91.28 | 92.54 | 92.64 |
| Thiorphan (%) | 0.08 | 0.13 | 0.07 | 0.09 | 0.06 | 0.05 |
| Benzyl Alcohol (%) | 1.3 | 1.29 | 1.3 | 1.11 | 1.22 | 0.87 |
| Impurity C (%) | 1.68 | 1.41 | 1.68 | 1.24 | 1.59 | 0.94 |
| Impurity G (%) | 0.96 | 7.42 | 1.14 | 5.73 | 1.33 | 4.93 |
| Solubility (mg/mL) | 2.62 | 2.43 | 2.41 | 2.39 | 2.26 | 1.92 |

Formula
1 - Captisol ® 60% w/w in pH 4.5 Acetate Buffer
2 - Captisol ® 60% w/w in pH 4.5 Citrate Buffer
3 - Captisol ® 70% w/w in pH 4.5 Acetate Buffer
4 - Captisol ® 69% w/w in pH 4.5 Citrate Buffer
5 - Captisol ® 78% w/w in pH 4.5 Acetate Buffer
6 - Captisol ® 80% w/w in pH 4.5 Citrate Buffer Test Methods
Sample Preparation:
1. Pipet 1 mL of Racecadotril solution into a 100 mL volumetric flask (V.F.)
2. Dilute to volume with the same buffer used in the solution preparation.
3. Further dilute the sample solution to about 0.1 mg/mL if necessary.

Sample Analysis
Inject standards (0.1 mg/mL of Racecadotril in Acetonitrile) and samples onto a suitable HPLC system under conditions similar to those suggested below. Parameters may be modified to optimize chromatography.

The assay of Racecadotril is determined by using the external standard injected. The degradation products levels are determined by % peak area relative to the Racecadotril peak.

Chromatographic conditions (European Pharmacopoeia Racecadotril method):

| Column: | Phenomenex Luna 5 μm C18 (2), 100 Å; 250 mm × 4.6 mm ID (Column ID in EP is 4.0 mm) |
|---|---|
| Column heater: | 30° C. |
| Wavelength: | 210 nm |
| Inj. Vol.: | 10 μL |
| Flow rate: | 1 mL/min |

Gradient Table:

| Time (min) | flow | % A | % B |
|---|---|---|---|
| Initial | 1.0 | 60 | 40 |
| 5 | 1.0 | 60 | 40 |
| 25 | 1.0 | 20 | 80 |
| 35 | 1.0 | 20 | 80 |
| 36 | 1.0 | 60 | 40 |
| 45 | 1.0 | 60 | 40 |

Mobil Phase A: Phosphate buffer, pH 2.5 (Buffer prep: dissolve 1 g of potassium dihydrogen phosphate in water, adjust to pH 2.5 with phosphoric acid, dilute to 1000 mL with water)

Mobil Phase B: 100% Acetonitrile

Stability of Racecadotril in Beta-Hydroxypropyl-Cyclodextrin (Beta-HPCD)

| | Time | Racecadotril | | | Benz Alcohol | | | Thiorphan | | | Impurity C | | | Impurity G | | |
|---|---|---|---|---|---|---|---|---|---|---|---|---|---|---|---|---|
| | | pH 3.6 | pH 4.0 | pH 4.5 | pH 3.6 | pH 4.0 | pH 4.5 | pH 3.6 | pH 4.0 | pH 4.5 | pH 3.6 | pH 4.0 | pH 4.5 | pH 3.6 | pH 4.0 | pH 4.5 |
| Acetate | Initial | 99.93 | 100.00 | 99.68 | 0.00 | 0.00 | 0.02 | 0.00 | 0.00 | 0.01 | 0.00 | 0.00 | 0.02 | 0.07 | 0.00 | 0.21 |
| | 1 week | 97.21 | 97.01 | 96.33 | 0.69 | 0.70 | 0.02 | 0.00 | 0.00 | 0.02 | 0.93 | 0.93 | 0.21 | 1.17 | 1.36 | 3.17 |
| | 2 week | 94.88 | 95.02 | 92.61 | 1.40 | 1.39 | 0.40 | 0.11 | 0.07 | 0.04 | 1.87 | 1.82 | 0.40 | 1.74 | 1.70 | 6.50 |
| | 3 week | 93.01 | 92.23 | 89.29 | 2.13 | 2.09 | 0.59 | 0.14 | 0.19 | 0.06 | 2.78 | 2.83 | 0.58 | 1.93 | 2.66 | 9.43 |
| | 4 week | 90.15 | 89.50 | 86.50 | 2.84 | 2.84 | 0.79 | 0.30 | 0.38 | 0.11 | 3.56 | 3.52 | 0.72 | 3.00 | 3.62 | 11.84 |
| | 6 week | 85.75 | 83.98 | 80.25 | 4.33 | 4.28 | 1.14 | 0.57 | 0.71 | 0.20 | 5.17 | 5.16 | 1.04 | 3.82 | 5.67 | 17.32 |
| | 8 week | 80.68 | 78.53 | 75.06 | 5.78 | 5.37 | 1.51 | 1.00 | 1.19 | 0.36 | 6.33 | 6.20 | 1.25 | 5.28 | 8.46 | 21.73 |

-continued

| | | Stability of Racecadotril in Beta-Hydroxypropyl-Cyclodextrin (Beta-HPCD) | | | | | | | | | | | | | |
|---|---|---|---|---|---|---|---|---|---|---|---|---|---|---|---|
| | | Racecadotril | | | Benz Alcohol | | | Thiorphan | | | Impurity C | | | Impurity G | | |
| | Time | pH 3.6 | pH 4.0 | pH 4.5 | pH 3.6 | pH 4.0 | pH 4.5 | pH 3.6 | pH 4.0 | pH 4.5 | pH 3.6 | pH 4.0 | pH 4.5 | pH 3.6 | pH 4.0 | pH 4.5 |
| Citrate | Initial | 99.91 | 100.00 | 99.71 | 0.00 | 0.00 | 0.02 | 0.00 | 0.00 | 0.01 | 0.00 | 0.00 | 0.01 | 0.09 | 0.00 | 0.19 |
| | 1 week | 96.45 | 95.93 | 96.44 | 0.79 | 0.89 | 0.22 | 0.00 | 0.00 | 0.01 | 0.98 | 1.23 | 0.18 | 1.78 | 1.95 | 3.15 |
| | 2 week | 92.01 | 93.19 | 93.19 | 1.72 | 1.41 | 0.40 | 0.13 | 0.11 | 0.03 | 2.30 | 1.82 | 0.36 | 3.81 | 3.47 | 6.04 |
| | 3 week | 88.22 | 89.81 | 90.20 | 2.59 | 2.36 | 0.59 | 0.31 | 0.21 | 0.06 | 3.36 | 2.82 | 0.52 | 5.52 | 4.79 | 8.66 |
| | 4 week | 84.51 | 86.78 | 87.41 | 3.38 | 2.79 | 0.79 | 0.47 | 0.40 | 0.10 | 4.23 | 3.43 | 0.62 | 7.38 | 6.57 | 11.16 |
| | 6 week | 77.91 | 80.70 | 82.05 | 5.09 | 4.19 | 1.14 | 1.11 | 0.85 | 0.17 | 6.13 | 4.98 | 0.90 | 9.72 | 9.24 | 15.86 |
| | 8 week | 71.51 | 75.46 | 77.34 | 6.64 | 5.54 | 1.51 | 1.80 | 1.42 | 0.29 | 7.54 | 6.22 | 1.11 | 12.47 | 11.26 | 19.95 |

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed:

1. A liquid composition comprising racecadotril and a sulfobutyl ether derivative of β-cyclodextrin;
    wherein the racecadotril is present in an amount of from about 0.10 grams to about 0.30 grams per 100 ml of the liquid composition;
    wherein the cyclodextrin is present in an amount of from about 5 grams to about 50 grams per 100 ml of the liquid composition;
    further comprising a buffer selected from the group consisting of a citrate, an acetate, a phosphate, and mixtures thereof;
    wherein chemical degradant products of racecadotril in the liquid composition are less than about 10% when stored at 3 months and 40° C.

2. The composition of claim 1, wherein the racecadotril is an RS racemic form or an R form.

3. The composition of claim 1, wherein the composition comprises a sweetener selected from the group consisting of sorbitol, high fructose corn syrup, sucralose, aspartame, saccharine, sucrose, and mixtures thereof.

4. The composition of claim 1, wherein the composition comprises a preseryatiye selected from the group consisting of sodium benzoate, potassium benzoate, propyl paraben, methyl paraben, butyl paraben, and mixtures thereof.

5. A dosage form, wherein the dosage form, comprises the composition of claim 1 delivered via a soft shell solid dosage form, a hard shell solid dosage form or a tablet dosage form.

6. The composition of claim 1, further comprising a second active ingredient that is a digestive health active ingredient.

7. The composition of claim 1, wherein the composition is delivered orally.

8. The composition of claim 1, wherein the composition has a pH of from about 3 to about 5 at 25° C.

9. A dosage form, wherein the dosage form comprises the composition of claim 8 delivered via a soft shell solid dosage form, a hard shell solid dosage form or a tablet dosage form.

10. The composition of claim 8, further comprising a second active ingredient that is a digestive health active ingredient.

11. A liquid composition comprising:
    about 0.1 wt. % to about 0.3 wt. % racecadotril;
    about 6 wt. % to about 8 wt. % a sulfobutyl ether derivative of β-cyclodextrin;
    about 16 wt. % to about 19 wt. % sorbitol;
    about 45 wt. % to about 55 wt. % high fructose corn syrup;
    about 0.1 wt. % to about 0.4 wt. % sodium chloride;
    about 0.1 wt. % to about 0.8 wt. % polyethylene glycol;
    about 15 wt. % to about 30 wt. % water; and
    about 0 wt. % to about 0.5 wt. % flavor,
    wherein each wt. % is based upon 100 ml of the composition.

12. A method for treating a subject experiencing diarrhea, comprising the step of orally administering to the subject a composition comprising racecadotril and a sulfobutyl ether derivative of (β-cyclodextrin.

13. The composition of claim 6, wherein the digestive health active ingredient is simethicone.

14. The composition of claim 10, wherein the digestive health active ingredient is simethicone.

15. The composition of claim 6, wherein the digestive health active ingredient is loperamide.

16. The composition of claim 10, wherein the digestive health active ingredient is loperamide.

17. The composition of claim 1, wherein the racecadotril is present in an amount of from about 0.25 grams per 100 ml of the composition.

18. The composition of claim 1, wherein the cyclodextrin is present in an amount of about 7 grams per 100 ml of the composition.

* * * * *